United States Patent [19]

Muto et al.

[11] 4,454,880
[45] Jun. 19, 1984

[54] NASAL HOOD WITH OPEN-BOTTOM MIXING CHAMBER

[76] Inventors: Rudolph Muto, 24 Williams St., Andover, Mass. 01810; Ronald Cotner, Box 96 R.F.D. No. 2, Chester, N.H. 03036

[21] Appl. No.: 377,340

[22] Filed: May 12, 1982

[51] Int. Cl.$^3$ .......................................... A61M 16/00
[52] U.S. Cl. ......................... 128/205.25; 128/207.13; 128/207.18
[58] Field of Search ..................... 128/207.13, 207.18, 128/203.18, 203.22, 206.24, 205.25

[56] References Cited

U.S. PATENT DOCUMENTS

| | | | |
|---|---|---|---|
| 1,331,297 | 2/1920 | Walker | 128/207.18 |
| 1,443,820 | 1/1923 | Hudson | 128/207.18 |
| 2,415,846 | 2/1947 | Randall | 128/206.24 |
| 2,675,803 | 4/1954 | Kaslow | 128/205.25 |
| 2,693,800 | 11/1954 | Caldwell | 128/207.18 |
| 4,354,488 | 10/1982 | Bartos | 128/207.13 |

Primary Examiner—Henry J. Recla
Attorney, Agent, or Firm—Pearson & Pearson

[57] ABSTRACT

An oxygen supply, hood for administering oxygen to a patient, departs from the enclosed masks and enlarged, open face shields, of the prior art by being formed as a unitary shell with a central dome, forming an open bottom, mixing chamber extending outwardly above the level of the mouth. The incoming oxygen forms a whirlpool, or vortex, within the chamber which mixes oxygen with moist exhaled air and permits the moist oxygen to also reach the mouth. The shell is firmly affixed by a recess over the bridge of the nose, by a strap across the upper lip and by a pair of integral wings, extending along the cheek bones to a band around the head. The gas delivery tube, within the mixing chamber extends under the nostrils, and along the upper lip of the patient. The gas discharge nozzles on the tube are directed only upwardly and outwardly, away from the nose and mouth, toward the inside face of the front wall of the shell.

5 Claims, 7 Drawing Figures

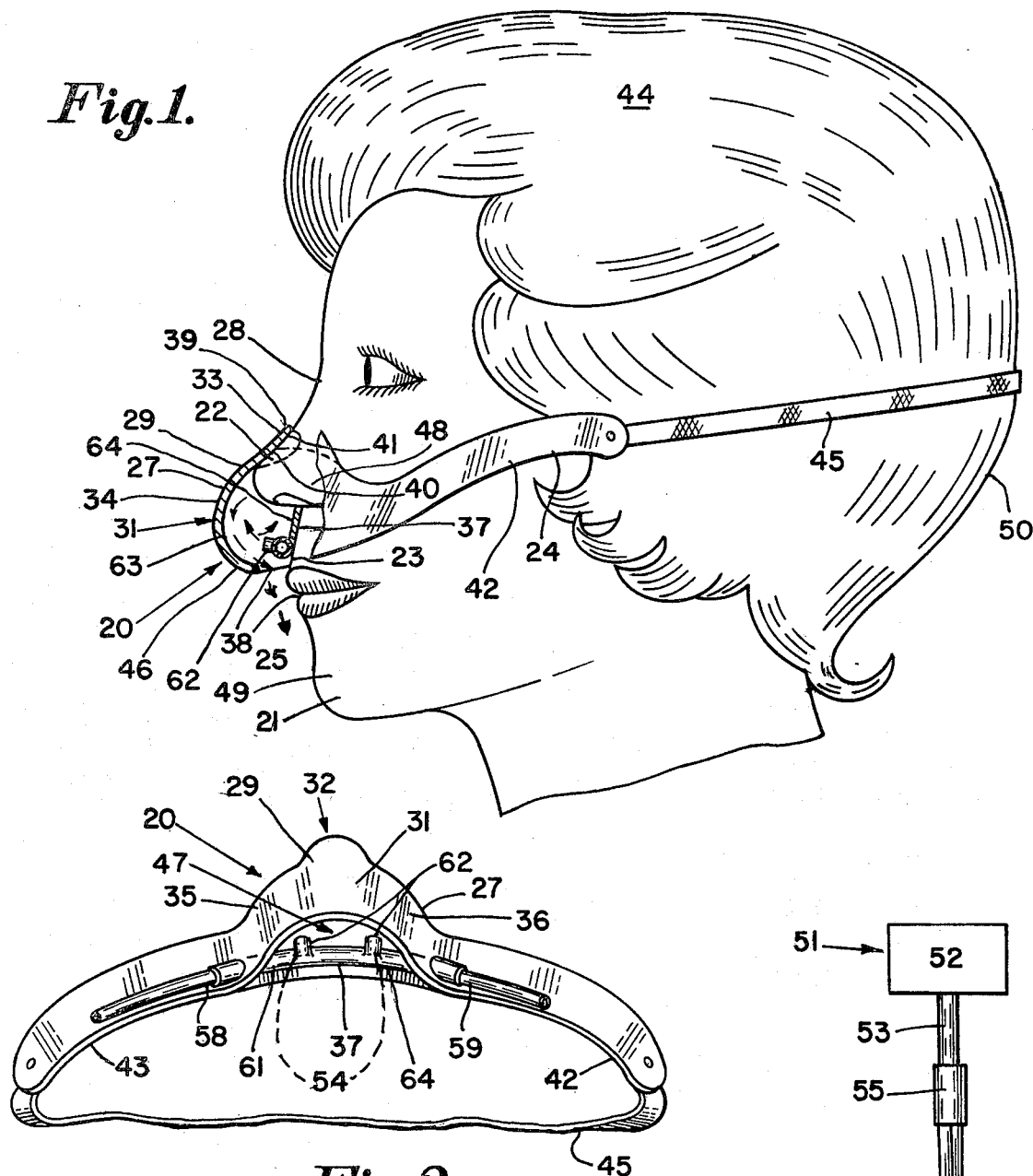
Fig.1.
Fig.2.
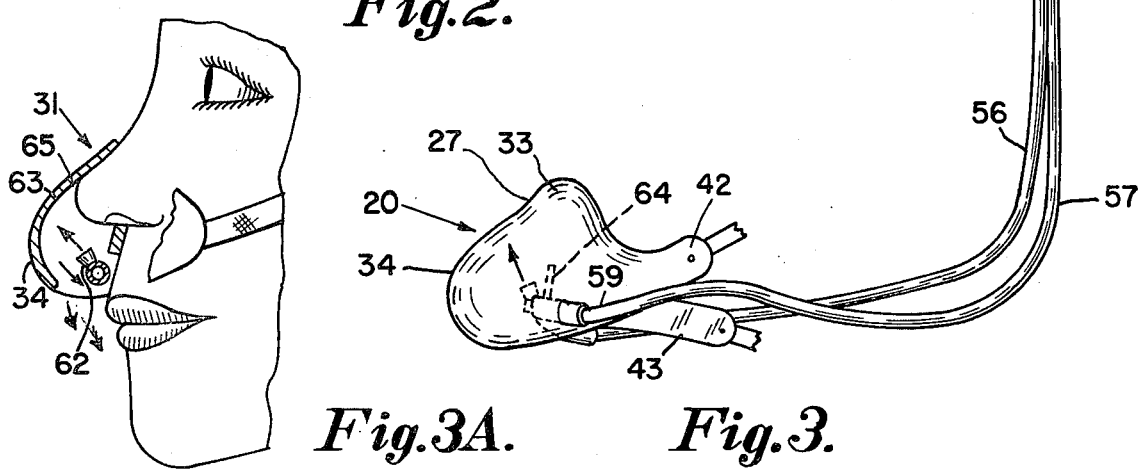
Fig.3A.   Fig.3.

NASAL HOOD WITH OPEN-BOTTOM MIXING CHAMBER

BACKGROUND OF THE INVENTION

It has heretofore been proposed to provide oxygen masks which form a cup like, enclosure over the nose of the patient so that apertures in an oxygen supply tube will discharge oxygen into the enclosed chamber of the mask for inhaling by the patient.

Exemplary of such devices are the masks disclosed in the following patents:

U.S. Pat. No. 1,288,647, Miller; Dec. 21, 1918
U.S. Pat. No. 1,632,449, McKesson; June 14, 1927
U.S. Pat. No. 2,843,121, Hudson; July 15, 1958
U.S. Pat. No. 2,843,122, Hudson; July 15, 1958
U.S. Pat. No. 2,859,748, Hudson; Nov. 11, 1958
U.S. Pat. No. 3,889,671, Baker; June 17, 1975
U.S. Pat. No. 4,354,488, Bartos; Oct. 19, 1982

The enclosed chambers of these masks, usually have one way air outlet valves in a side, or bottom wall but they tend to build up heat, fear of asphyxiation and possibly can cause suffocation due to vomitting.

In U.S. Pat. No. 4,263,908 to Mizerak of Apr. 28, 1981 a nasal cannula mask is disclosed which has an enclosed chamber fitting over the mouth and is supported on the chin of the wearer.

Another known device for administering oxygen is marketed as "The Face Shield" by Hudson Oxygen Therapy Sales Co. of Temecula, Calif. It does not have an enclosed cup-like chamber, but instead is an open bottom skirt which extends from the bridge of the nose down to the level of the bottom of the chin with apertures in the front wall facing upwardly and rearwardly from the level of the lower lip toward the nostrils. This device is of such large area that fixation without leakage to the eyes presents problems, especially if the patient rolls over, or the lower tip of the mask is inadvertently struck. Fixation is by elastic straps over the ears and a strip of moldable metal which is intended to be molded by the fingers to fit over the bridge of the nose.

The Bartos nose mask of U.S. Pat. No. 4,354,488, discloses a shell with a gas delivery tube having gas delivery openings within the shell directed in any of a variety of directions usually toward the mouth or nose. It also teaches that the gas delivery tube should be below the tip of the wearers nose, and not under the nostrils, so that the area under the nose is completely open.

SUMMARY OF THIS INVENTION

In this invention there is no cup shaped mask with enclosed chamber fitting over the nose and no air outlet holes or valves, but instead the device is what we call a hood, shroud or dome forming an open-bottom chamber, the dome projecting outwardly, from upper lip level, for a spaced distance to mix incoming oxygen with moist exhaled breath in a whirlpool, or vertical circulation, turbulent manner. Because the dome and its open bottom chamber are at nostril and upper lip level they do not interfere with eating, drinking, talking, or breathing through the mouth nor do they build up heat or collect vomit issued from mouth or nostrils.

The oxygen supply manifold within the chamber, is connected to a supply of oxygen, and extends across the open bottom chamber from side wall to opposite side wall, resting along the upper lip with the pair of oxygen discharge ports, or nozzles directed outwardly and upwardly against the inside face of the front wall of the dome-like shell. This creates the whirlpool vortex circulation which mixes the oxygen with moist exhaled air and fills the chamber as well as circulating through the open bottom down to in front of the mouth for inhalation through the mouth.

Three point fixation is obtained by a central recess in the upper central portion of the dome which seats on the bridge of the nose, by a narrow strap, or by the manifold of the tube, resting along the upper lip and by a pair of rearwardly and upwardly extending wings, integral with the shell and each extending along one of the opposite cheek bones for attachment by an elastic band around the rear of the head.

The continuous, whirlpool vortical path of moist oxygen within the open bottom chamber of the dome of the shell of the hood of the invention creates a globular path part of which is always in front of the mouth and is much preferred to what might be called an anatomical chamber covering both nose and mouth and in which the oxygen is trapped. Non-humidified oxygen jetted into the nostrils may dry and burn the sensitive nasal mucous and causes patient discomfort at high flow rates due to the jet stream.

In addition, the points of stabilization being the cheek bones, upper lip and bridge of the nose, there is virtually no possibility of nasal and/or septal necrosis occasionally seen when prongs into the nostrils are used to stabilize the cannula.

BRIEF DESCRIPTION OF THE DRAWINGS

FIG. 1 is a side elevation of a human head with the nasal hood of the invention in place and in half section, FIG. 2 is a bottom plan view of the hood, FIG. 3 is a side elevation of the hood, FIG. 3A is a close-up view of the hood in half section.

DESCRIPTION OF A PREFERRED EMBODIMENT

Figure 4:
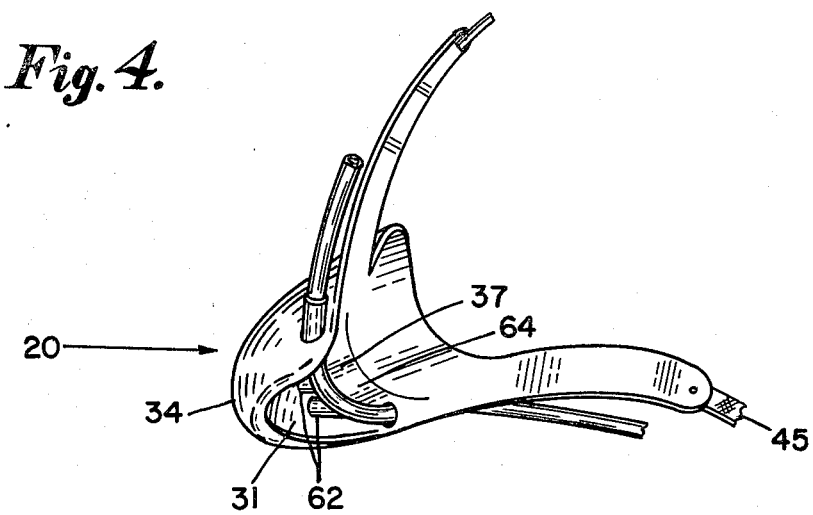
FIG. 4 is a perspective view of the hood looking up into the mixing chamber.
Figure 5:
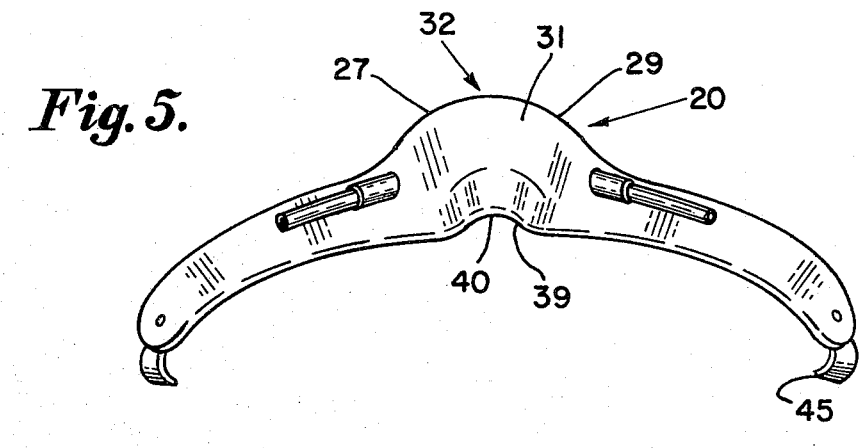
FIG. 5 is a top plan view of the hood and FIG. 6 is an enlarged, perspective rear view showing the inside of the mixing chamber and the oxygen discharge nozzles and manifold.
Figure 6:
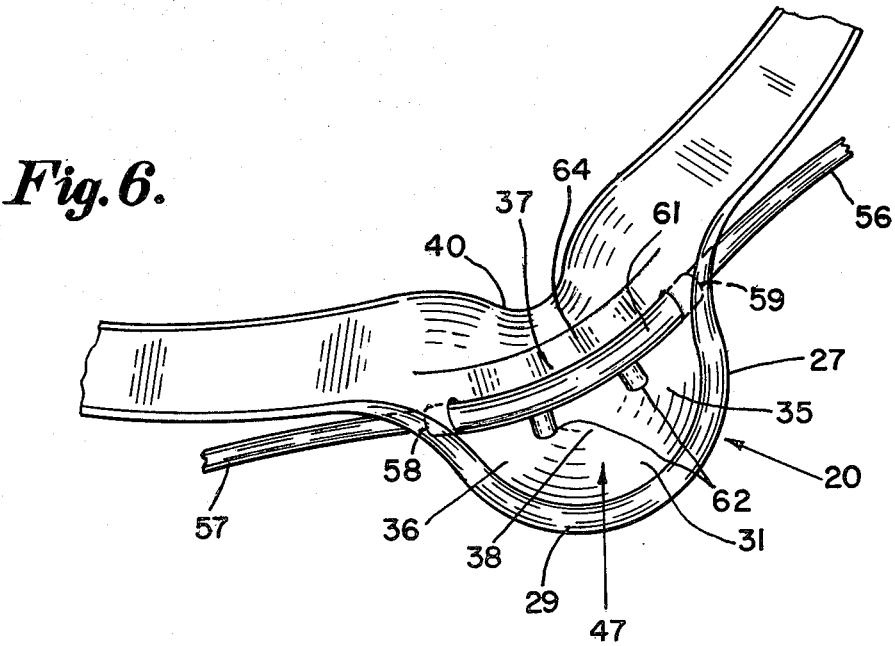

As shown in the drawings, the nasal hood 20 of the invention is not a face shield covering the face and is not a cup shaped mask edge sealed against the face of a patient 21. Nasal hood 20 could be described as a shroud, cover, or roof, at the level of the nose 22, upper lip 23 and cheek bones 24 of the patient.

Thus it does not interfere with eating, drinking talking or breathing through the mouth 25 and does not interfere with sight through the eyes 26.

Nasal hood 20 is preferably formed of soft, pliable, gas impermeable material 27, which may be plastic and translucent and such that it may be sterilized for reuse. The plastic material 27 is relatively thin, flexible and resilient so as to conform to the configuration of the face 28 of a patient and is non-toxic, light in weight, and preferably polyethylene, or the like.

Nasal hood 20 comprises a shell 29, having a dome 31, in the central portion 32, the dome having a top wall 33, front wall 34, side walls 35 and 36, a rear opening 37 and a bottom opening 38.

The upper edge 39 of top wall 33 is thin, soft, resilient and pliable to conform to the configuration of the face of the patient 21 and seal the edge against leakage of oxygen out of dome 31 into the eyes 26 to cause irritation, or other eye damage. A recess 40 is formed in the central portion of top wall 33 to fit over the bridge 41 of nose 22 and conform to the shape thereof while acting as a seal.

Each opposite side wall 35 or 36 includes an integral, elongated side wing, or flap, 42 or 43 which extends along the cheek bones, such as 24, of the head 44 of the patient. An elastic band 45 connects the ends of the wings 42 and 43 around the back of the head 50 of the patient.

The front wall 34 is provided with a slightly inturned, curved, lower edge 46, which defines part of the rim of the bottom opening 38 of the mixing chamber 47 formed within the dome 31 of shell 29. It will be seen that the open bottom dome 31 and the open bottom mixing chamber 47 are located at the level of the nostrils 48 and upper lip 23 of the patient 21 with no part extending down to the level of mouth 25 or chin 49 to interfere with eating, drinking, breathing or talking through the mouth. The dome 31 extends outwardly away from upper lip 23 and nostrils 48 to position mixing chamber 47 just above the level of the mouth.

Oxygen, or other gas supply means 51 includes a source 52 connected to an oxygen tube 53 which may run along one of the wings 42 or 43 and into the mixing chamber 47, there being oxygen discharge apertures 54 within the mixing chamber. Preferably, however, tube 53 is divided at a coupling 55 into two branch supply tubes 56 and 57, each extending along a wing 42 or 43 and each having a terminal end 58 or 59 sleeved into one of the opposite ends of a manifold tube 61.

The manifold tube 61, preferably includes a pair of spaced nozzles 62 each at an each aperture 54, the nozzles or apertures being located along the bottom of the rear opening 37 and directed toward the inside face 63 of the front wall 34 of open bottom dome 31. Thus, the oxygen does not directly jet into the nostrils 48 to possibly burn and dry the nasal mucous, or to cause nasal and septal necrosis.

Instead, the incoming oxygen is mixed with moist air being exhaled by the patient while its direction of flow within the open bottom mixing chamber 47 creates a vortical circulation, or whirlpool effect for thorough mixing before being inhaled as moist oxygen. The swirling turbulence of moist oxygen in the mixing chamber also enables a portion of the moist oxygen to escape through the open bottom down to the mouth area for inhalation through the mouth of humidified oxygen.

The manifold 61, or the apertured part of tube 53, preferably extends along, and rests against the upper lip portion of the patient's face for additional stabilization and fixation or it may be accompanied by a narrow strap 64 which extends across the bottom of the rear opening 37 from one side wall 35 to the other side wall 36 to support the shell 29 thereon.

Thus the nasal hood of the invention has three point fixation, namely the strap 64, tube 53 or manifold 61 along the upper lip, the recess 40 in the upper edge 39 of the shell and the wings or flaps 43 and 44 extending along the cheek bones for attachment behind the head 44 of the patient 21.

Preferably oxygen is introduced into the open bottom dome 31 of hood 20, from nozzles 62 at a rate of about six to eight liters per minute but because directed outwardly against inner wall 63 rather than jetted at the nostrils, the whirlpool effect prevents any damage, or discomfort, to the patient.

As best shown in FIG. 3a, it may be desirable to aim the nozzles 62 at the top 65 of the inside face 63, of the front wall 34 of the dome 31, to achieve a turbulence within the dome without directly jetting at the nostrils and still enable moist oxygen to readily reach the mouth 25. The inturned, curved lower edge 46 and the integral side wings, or flaps, 42 and 43 may also be reduced in size, or eliminated, but it is preferred that they be provided as shown in the other figures of the drawings.

We claim:

1. A nasal hood for administrating oxygen to a patient, said hood comprising:

a shell of soft, flexible imperforate material shaped to fit over and cover the nose of a patient while leaving the patient's mouth free to eat, drink, or breath;

said shell having a top wall, opposite side walls, a front wall, a rear opening, to accommodate the nose of the patient, and a bottom opening for exhalation of air, said front wall having a lower edge slightly inturned and said shell forming an open bottom dome adapted to project outwardly, above the level of the mouth of said patient, to form a mixing chamber;

the side walls of said shell having integral wings, each adapted to extend along the cheek bones of said patient for fixation by a band around the back of the head of patient;

and an oxygen supply tube, connectable to a source of oxygen, and extending along one of said wings, through said sidewall of said shell and into the mixing chamber of said dome, and positioned to be under the nostrils, and along the upper lip of the patient said tube having discharge nozzles directed only upwardly and outwardly away from the nose and mouth of the patient toward the front wall of said shell and adapted to create vortical circulation of incoming oxygen within said chamber;

said shell including a narrow strap connected to said opposite sidewalls and extending from one side wall to the other, across said rear opening so as to extend along the upper lip of the patient for additional firm fixation of said hood;

whereby said oxygen is mixed with moist air exhaled by said patient and some of said moist oxygen may be inhaled through the mouth of said patient.

2. A nasal hood as specified in claim 1 wherein:

said shell includes a thin, soft flexible upper edge arranged to flexibly seal the same against the skin below the eyes, to prevent oxygen from reaching the eyes of the patient, and a central recess fitting over the bridge of the nose.

3. A nasal hood as specified in claim 1 wherein:

said oxygen supply tube is divided into two branches, each branch extending along one of said integral wings and includes a sleeve having opposite ends extending through respective sidewalls of said shell, said sleeve containing said discharge nozzles, each branch being sleeved into one of the opposite ends of said sleeve.

4. A nasal hood comprising:

a shell of imperforate material having a central portion formed as an open bottom dome adapted to sealingly fit over the nose, below the eyes of a patient and to form an open bottom mixing chamber above the level of the mouth, and projecting outwardly from the face of a patient;

said shell having a pair of integral side wings extending rearwardly therefrom and adapted to be supported on the cheek bones for fixation by a band around the back of the head, a narrow strap connected to said shell and extending from one side of said dome to the other and adapted to rest on the upper lip portion of a patient and having an upper central recess conforming to the shape of, and closely fitting over, the bridge of the nose of a patient for fixation of said shell;

oxygen supply means including an oxygen supply tube connected to said shell and adapted to extend under the nostrils, along the upper lip of the patient within the mixing chamber of said open-bottom dome and having a pair of spaced apart oxygen discharge nozzles directing incoming, pressurized, oxygen away from the mouth and nose and only upward and outward in a direction to form a vortex within said chamber for mixing oxygen with moist exhaled air and directing some moist oxygen down into the mouth area of the patient;

said shell having a top wall with an upper edge which is thin, soft, resilient and pliable to conform to the configuration of the face of a patient and seal and the edge against leakage of oxygen into the eyes of the patient.

5. A nasal hood comprising:

a shell arranged to cover the nose of a patient while sealing the eyes against flow of oxygen and freeing the mouth to eat, drink, and breath;

said shell having a central dome, adapted to extend outwardly away from the upper lip, above the level of the mouth, said dome having side walls, a front wall with a slightly inturned curved lower edge, and forming an open-bottom, mixing chamber, when said shell is affixed on a patient; and oxygen supply means including a tube connected to said shell and leading from a source of oxygen into said chamber and adapted to extend under the nostrils and along the upper lip of the patient and having apertures within said chamber directed only upwardly and outwardly against front wall to create a vortex therewithin for mixing oxygen with moist exhaled air;

a pair of wings, integral with said shell, and each arranged to extend along one of the opposite cheek bones of said patient, for affixation by a band around the back of the head of said patient; and a narrow strap, integral with, and extending from each opposite side wall of said shell, across said chamber, and adapted to rest along the upper lip portion of said patient for firm affixation of said shell;

said shell including an upper edge of soft, deformable material for conforming to the contour of the face of said patient below the eyes, said edge including a central recess shaped to fit over the bridge of the nose for firmly affixing said mask while sealing said edge against leakage of oxygen to the eyes of said patient.

* * * * *